United States Patent
Lampropoulos et al.

(10) Patent No.: US 6,170,785 B1
(45) Date of Patent: Jan. 9, 2001

(54) MANIFOLD ADAPTOR BRACKET

(75) Inventors: Fred P. Lampropoulos; William Padilla; Bryan R. Lampropoulos, all of Sandy, UT (US)

(73) Assignee: Merit Medical Systems, Inc., Sandy, UT (US)

( * ) Notice: Under 35 U.S.C. 154(b), the term of this patent shall be extended for 0 days.

(21) Appl. No.: 09/241,331

(22) Filed: Feb. 1, 1999

(51) Int. Cl.[7] ................................................. A47G 29/00
(52) U.S. Cl. ................................ 248/220.21; 248/222.13
(58) Field of Search .......................... 248/220.21, 689, 248/205.3, 223.41, 229.21, 231.31, 235, 250, 506, 688, 314

(56) References Cited

U.S. PATENT DOCUMENTS 5,411,705 * 5/1995 Thor et al. .......................... 422/45
5,829,723 * 11/1998 Brunner et al. ................. 248/222.13

* cited by examiner

Primary Examiner—Anita M. King
(74) Attorney, Agent, or Firm—Workman, Nydegger & Seeleyt

(57) ABSTRACT

An adaptor bracket for selectively coupling a manifold to a medical device has (i) a tab having a first end and a second end; and (ii) first and second gripping fingers extending from the second end of the tab. The first end of the tab is configured to be coupled to the medical device. The first and second gripping fingers are spaced so as to selectively receive a portion of a manifold within a groove formed between the first and second gripping fingers. The configuration of the bracket enables convenient manipulation of valves and ports on the manifold, such as when the practitioner desires to exchange tubing on the mounted manifold.

18 Claims, 5 Drawing Sheets

MANIFOLD ADAPTOR BRACKET

BACKGROUND OF THE INVENTION

1. The Field of the Invention

This invention relates to fluid flow manifolds coupled to medical devices. More specifically, this invention relates to a bracket used to connect a manifold to a venous reservoir of a medical bypass system.

2. The Relevant Technology

Manifolds are employed in a variety of different procedures including, for example, heart/lung bypass procedures, and a wide variety of procedures in which it is desired to control a number of different fluids flowing to or from a patient. One example of such a manifold is the prior art manifold 10 shown in FIG. 1.

Manifold 10 has a fluid flow tube 12 for transporting a variety of different pressure laden fluids through manifold 10. Valves 16 are coupled to the tube 12 such that the stopcocks 14 of valves 16 selectively direct fluid between tube 12 and ports 17 of respective valves 16. Ports 17 are selectively coupled through tubes to a variety of different systems and fluid containers. Valves 16 of manifold 10 are joined to a plate 18. A cushioned adhesive material 19 is disposed below plate 18.

With reference now to FIGS. 1–3, it is common for manifold 10 to be coupled to a venous reservoir 20 during a medical procedure. Examples of such medical procedures include bypass procedures, specifically heart-lung bypass procedures in which various fluids are injected through ports 21 in the lid 22 of a reservoir 20 into the body 23 of the reservoir 20. The fluids then flow through a port (not shown) in the bottom of reservoir body 23 to the patient, e.g., through a continual drip process. Reservoir 20 is employed in conjunction with an oxygenator system.

Since a variety of different fluids converge into reservoir 20, reservoir 20 acts as a central operational station for the collection and control of fluids during a bypass procedure. Consequently, mounting manifold 10 onto reservoir 20 enables control of fluid flow from a central location without commingling the fluid within manifold 10 with the fluid in reservoir 20. Manifold 10 may be desired for monitoring certain vital fluids when the ability to control the flow of such vital fluids is at a premium, for example.

By coupling manifold 10 to a stable object, manifold 10 does not need to be held by a practitioner. In order to couple manifold 10 to reservoir 20, the lid 22 of reservoir 20 has a socket 24 thereon for receiving the plate 18 of manifold 10. Socket 24 is coupled to lid 22 adjacent a peripheral edge 25 of lid 22.

However, manifold 10 is difficult to insert into socket 24. In addition, once coupled to reservoir 20, it is difficult for the practitioner to manipulate the stop-cocks 14 and ports 17 of manifold 10. One reason for this difficulty is the proximity of manifold 10 to lid 22 of reservoir 20. Particularly when a practitioner is wearing gloves covered with fluid such as blood, medicament, or contrast fluid, it is difficult to grasp ports 17 or stop-cocks 14. Lid 22 of reservoir thus interferes with any attempt to insert or remove manifold 10 from socket 24 or to manipulate stopcocks 14 or ports 17 while manifold 10 is disposed within socket 24.

For example, particularly when a sterile field must be maintained and the practitioner is required to wear gloves covered with fluid, it is difficult to exchange tubing on ports 17 while plate 18 is positioned within socket 24. In such circumstances, practitioners are sometimes required to remove manifold 10 from socket 24 in order to couple or decouple such tubes or other devices to manifold 10. The practitioner is then required to replace manifold 10 within socket 24, which is again a difficult process.

Optionally, the practitioner removes a used manifold 10, discards the used manifold 10, then couples the tubes or other devices to the new, clean manifold 10 and inserts the new manifold 10 into socket 24. This option, however, is time consuming and highly inefficient from a cost and supply standpoint.

Yet another difficulty with manifold 10 is that manifold plate 18 is unstable, wobbling with respect to lid 22. This difficulty is ameliorated somewhat by the placement of a cushioned adhesive strip 19 under plate 18. The adhesive strip 19 may be used in an attempt to secure plate 18 to lid 22. However, strip 19 can lose its adhesion, particularly in the center of strip 19 and particularly after repeated recoupling of manifold 10 to lid 22. This can cause strip 19 to be positioned above the lid 22, as shown in FIG. 3.

Even if the strip 19 does not lose its adhesion, the adhesive nature of strip 19 can complicate coupling and decoupling of plate 18 to socket 24. In addition, the requirement of an adhesive material in addition to the rigid material used for plate 18 adds expense and complicates the manufacturing process. Furthermore, the proximity of both plate 18 and valves 16 to lid 22 makes the entire manifold 10 susceptible to damage from lipids or other fluids leaking onto lid 22.

SUMMARY AND OBJECTS OF THE INVENTION

It is therefore an object of the invention to provide an improved medical system.

It is another object of the invention to provide an improved manifold adaptor bracket.

It is another object of the invention to provide a manifold adaptor bracket which enables convenient access to ports and valves on the manifold when the adaptor bracket and manifold are coupled to a medical device, such as a venous reservoir.

It is another object of the invention to provide a manifold adaptor bracket configured to selectively receive the manifold.

It is another object of the invention to provide a manifold adaptor bracket configured to be selectively coupled to a receiving socket of a venous reservoir.

An adaptor bracket of the present invention is used to connect a manifold device having a plurality of valves to a medical device. The adaptor bracket comprises a tab having (i) a first end and a second end; and (ii) first and second gripping fingers extending from the second end of the tab. The first end of the tab is configured to be coupled to the medical device. Preferably, the first end is configured to be selectively inserted within a receiving socket on the lid of a venous reservoir of a medical bypass system.

The first and second gripping fingers are spaced, thereby forming a groove between the first and second gripping fingers. The fingers selectively receive a portion of a manifold within the groove in a tight fitting relationship. The gripping fingers allow a manifold to be grasped and manipulated in a convenient manner.

The configuration of the adaptor bracket creates a significant space between a manifold and the lid of the reservoir on which a receiving socket is mounted. This enables convenient manipulation of stop-cocks, valves, and ports, such as when exchanging tubing on the ports. The adaptor bracket extends a face of at least one port on at least one of the valves of the manifold vertically and horizontally away from a peripheral edge of the lid.

The adaptor bracket further comprises first and second aligning fingers extending from the first gripping finger for aligning the first and second gripping fingers with respect to a valve on the manifold. This enables a convenient snap-on coupling and aligning of the manifold onto a bracket.

Also in a preferred embodiment, at least one and preferably two ridges are located on an opposing side of the second end of the tab from the first and second fingers. These ridges stabilize the tab by touching the surface adjacent a socket, preventing the wobbling, chattering or other movement of the tab with respect to the surface. The ridges do not interfere with the coupling or decoupling of the tab from the socket and will not lose their stabilizing ability over time.

Since the adaptor bracket is selectively coupled to the manifold, the adaptor bracket and manifold can be made from different materials. For example, it may be desirable to manufacture the adaptor bracket from a lipid-compatible material, while manufacturing the manifold from another material which does not require such compatibility. Another advantage of the adaptor bracket of the present invention, is that it can be retrofit onto a variety of different manifolds.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 4:
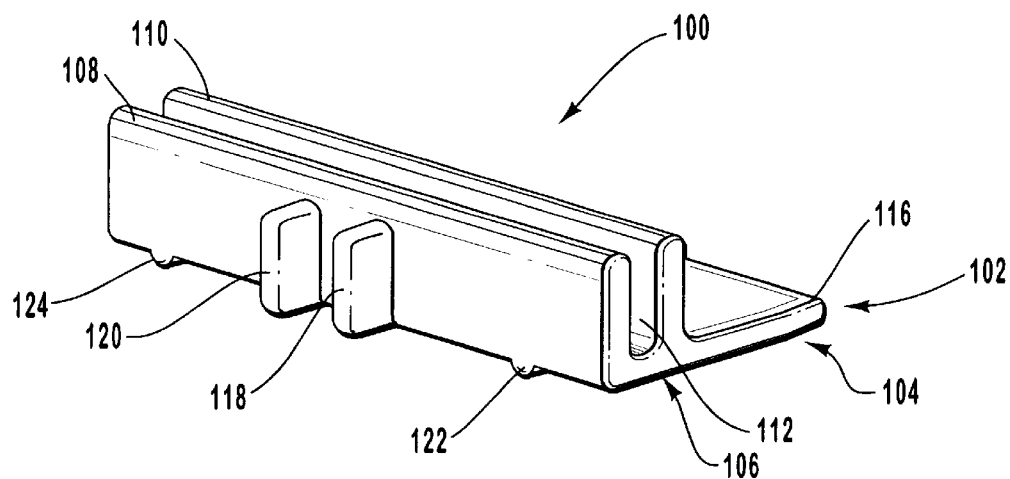
FIG. 4 is a frontal perspective view of a manifold adaptor bracket of the present invention.
Figure 5:
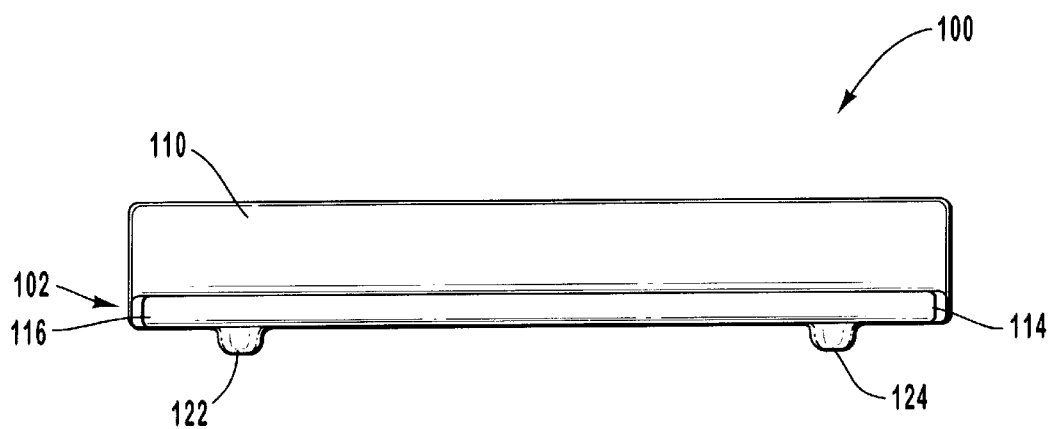
FIG. 5 is a rear view of the manifold adaptor bracket of FIG. 4.

With reference now to FIGS. 4 and 5, an embodiment of a manifold adaptor bracket 100 of the present invention is shown. Adaptor bracket 100 selectively couples a manifold having a plurality of valves to a medical device having a body and a lid. A receiving socket is preferably mounted on the lid of the device for receiving a portion of adaptor bracket 100.

Manifold adaptor bracket 100 comprises a tab 102 having (i) a first end 104 and a second end 106; and (ii) first and second gripping fingers 108, 110 extending from second end 106 of tab 102. First and second gripping fingers 108, 110 are spaced, thereby forming a groove 112 between first and second gripping fingers 108, 110. Fingers 108, 110 selectively receive a portion of a manifold within groove 112.

First end 104 is configured to be coupled to a medical device. Preferably, first end 104 is configured to be selectively coupled to a venous reservoir of a medical bypass system by being inserted within a receiving socket on the lid of the reservoir. In order to facilitate such insertion, first end 104 of tab 102 is preferably tapered on opposing edges 114, 116 thereof.

Tab 102 preferably comprises a substantially rectangular shaped plate, although a variety of different tabs are available, such as a tab having a tubular shape, a rounded shape, a cylindrical shape, a square shape, an elongated shape, a tab having the shape of a beam or a variety of shapes which are configured to fit within a receiving socket.

First and second gripping fingers 108, 110 extend upwardly from tab 102. This configuration creates space between the manifold and the lid of the reservoir or other object on which the receiving socket is mounted. Preferably, adaptor bracket 100 extends the faces of the ports on the valves of a manifold vertically and horizontally away from a peripheral edge of the lid of the medical device, making adjustments to the ports and stopcocks convenient. In addition, first end 104 of tab 102 is preferably configured to be selectively inserted within the receiving socket such that tab 102 is substantially parallel with the lid, also making adjustment of ports and stopcocks convenient. These relationships are illustrated by way of example in FIGS. 6-8 and discussed in additional detail below.

With continued reference to FIGS. 4 and 5, also in a preferred embodiment, first and second gripping fingers 108, 110 extend integrally from tab 102. Although such integral coupling is not required, and coupling thereof can occur through an adhesive or other bond, this integral configuration permits convenient manufacturing of adaptor bracket 100, such as through injection molding. The integral configuration also provides a strong, rigid connection between fingers 108, 110 and tab 102. Thus, first and second fingers 108, 110 extend substantially rigidly from tab 102 when a portion of a manifold is disposed between first and second fingers 108, 110.

Fingers 108, 110 receive the portion of the manifold in a tight-fitting relationship within groove 112. This tight-fitting relationship is convenient because no moving parts are required to couple the manifold and adaptor bracket 100 and because bonding between the manifold and adaptor bracket 100 is not required. Nevertheless, a strong connection is maintained during use. Adaptor bracket 100 further comprises first and second aligning fingers 118, 120 extending from first gripping finger 108 for aligning first and second gripping fingers with respect to a valve on the manifold.

Also in a preferred embodiment, at least one and preferably two ridges 122, 124 are located on an opposing side of second end 106 of tab 102 from first and second fingers 108, 110. Ridges 122, 124 stabilize tab 102 by touching the surface adjacent a socket, preventing wobbling, chattering or other movement of tab 102 with respect to the surface. In one embodiment, ridges 122, 124 are approximately the same height as the bottom plate 125 of a socket 24 (shown in FIG. 6). A variety of different sizes and configurations of a tab and gripping fingers may be employed, such as a larger or smaller plate, or larger or smaller fingers.

Figure 6:
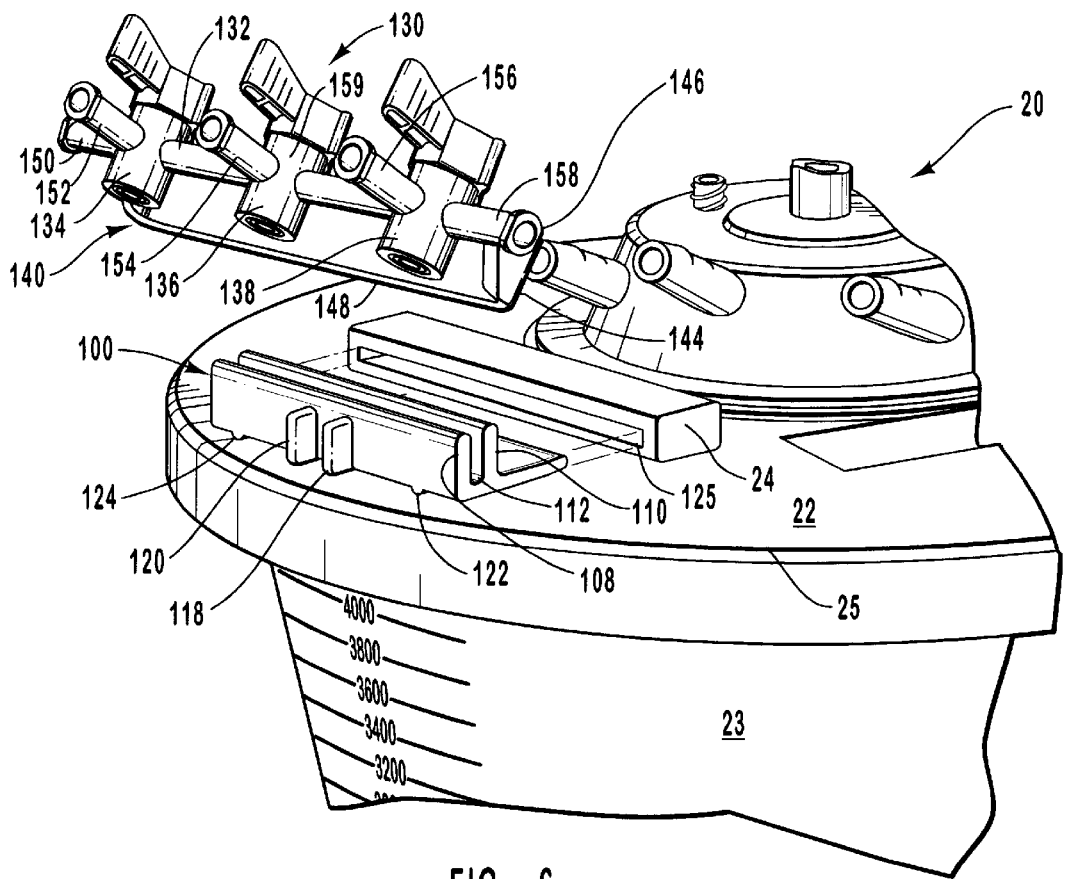
FIG. 6 is a view of a manifold shown adjacent the manifold adaptor bracket of FIG. 4, each of which are shown adjacent a socket on a venous reservoir.

With reference to FIG. 6, an example of a manifold 130 is shown. Although a variety of different manifolds may be coupled by adaptor bracket 100 to socket 24, the manifold is required to have a portion thereof which fits between gripping fingers 108, 110.

The manifold may accomplish such a goal in a variety of different manners. In one embodiment, the fluid flow tube of the manifold is configured to fit within and be held by gripping fingers 108, 110. In another embodiment, a valve or port of the manifold is configured to fit within fingers 108, 110. In another embodiment, a support plate or flange or other support member extending from the manifold is configured to fit within fingers 108, 110.

Manifold 130 shown in FIG. 6 is one example of a manifold which can be selectively coupled to adaptor bracket 100. Manifold 130 comprises a fluid flow tube 132 and first, second and third valves 134, 136, 138 coupled in fluid communication with fluid flow tube 132. Valves 134, 136, 138 each have at least one fluid flow port having a face. Ports 150, 152 of valve 134, port 154 of valve 136 and ports 156, 158 of valve 138 are selectively coupled to tubes, catheters, or ports of other structures or devices. Valves 134, 136, 138 are stopcock-actuated valves. A variety of different valves and numbers of valves may be employed in a manifold compatible with adaptor bracket 100, however.

Manifold 130 further comprises a support member 140 coupled to valves 134, 136, 138 and tube 132. Support member 140 comprises a rigid support plate 142 (see FIG. 7) coupled at one end to tube 132 and valves 134, 136, 138, and a flange 144 coupled to an opposing end of plate 142. First and second sides 146, 148 of flange 144 are positioned to extend outwardly from opposing sides of plate 142. The first and second sides 146, 148 of flange 144 are preferably each oriented at approximately a right angle from plate 142, although a variety of different orientations are possible. Since, in one embodiment, manifold 130 only employs one side of flange 144, each side 146, 148 itself serves as an example of an individual flange coupled to plate 142.

These sides 146, 148 of flange 144 serve as convenient portions of manifold 130 to be selectively coupled to adaptor bracket 100. Gripping fingers 108, 110 receive flange 144 such that support plate 142 is substantially parallel to the lid. Consequently, valves 134, 136, and 138 are convenient to actuate and ports 150, 152, 154, 156 and 158 of respective valves are readily and conveniently accessible for the placement of tubes thereon. However, a plate without a flange coupled thereto may also be selectively coupled to adaptor bracket 100, for example.

First and second gripping fingers 108, 110 of adaptor bracket 100 are preferably configured to selectively receive a support member 140 of manifold 130 as discussed above. One side 148 of flange 144 is disposed within groove 112 formed between gripping fingers 108, 110. Preferably side 148, which is opposite the stop-cock handles, is disposed within groove 112. This permits convenient use of the stop-cock handles.

Figure 7:
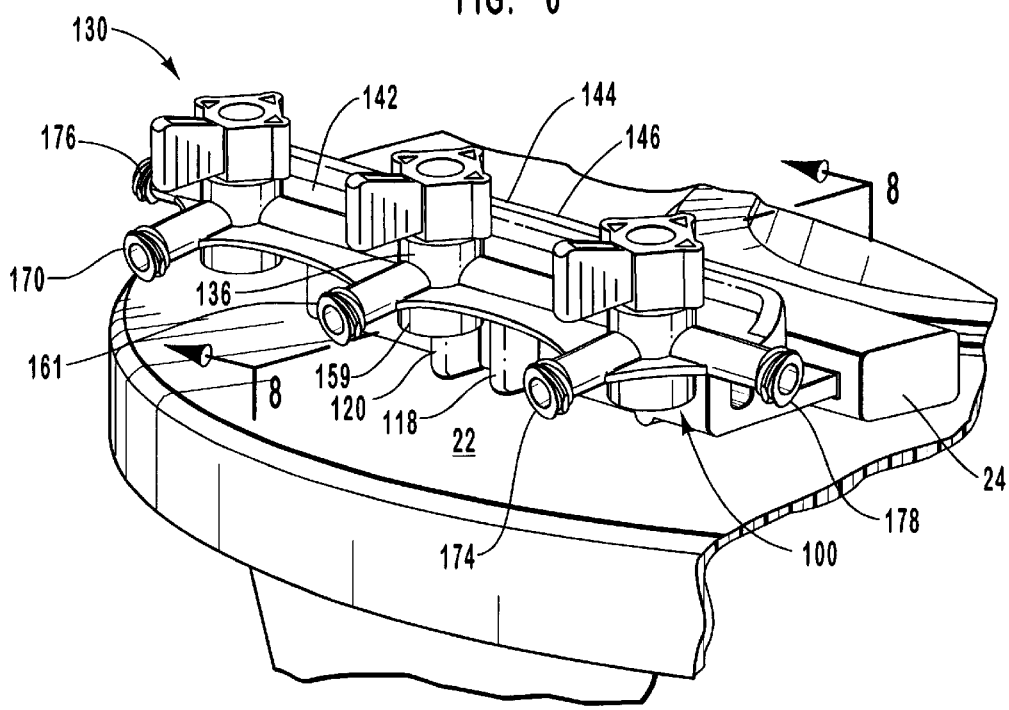
FIG. 7 is a view of the adaptor bracket of FIGS. 4–6 coupling the manifold of FIG. 6 to the socket of the venous reservoir.

As shown in FIG. 7, a snap-on alignment of manifold 130 to adaptor bracket 100 is facilitated through the use of first and second aligning fingers 118, 120. Aligning fingers 118, 120 are snapped onto opposing sides of the valve casing 159 of middle valve 136. This snap-on alignment centers adaptor bracket 100 in a desired position on flange 144. In addition, the alignment automatically orients the stop-cocks away from adaptor bracket 100.

Figure 1:
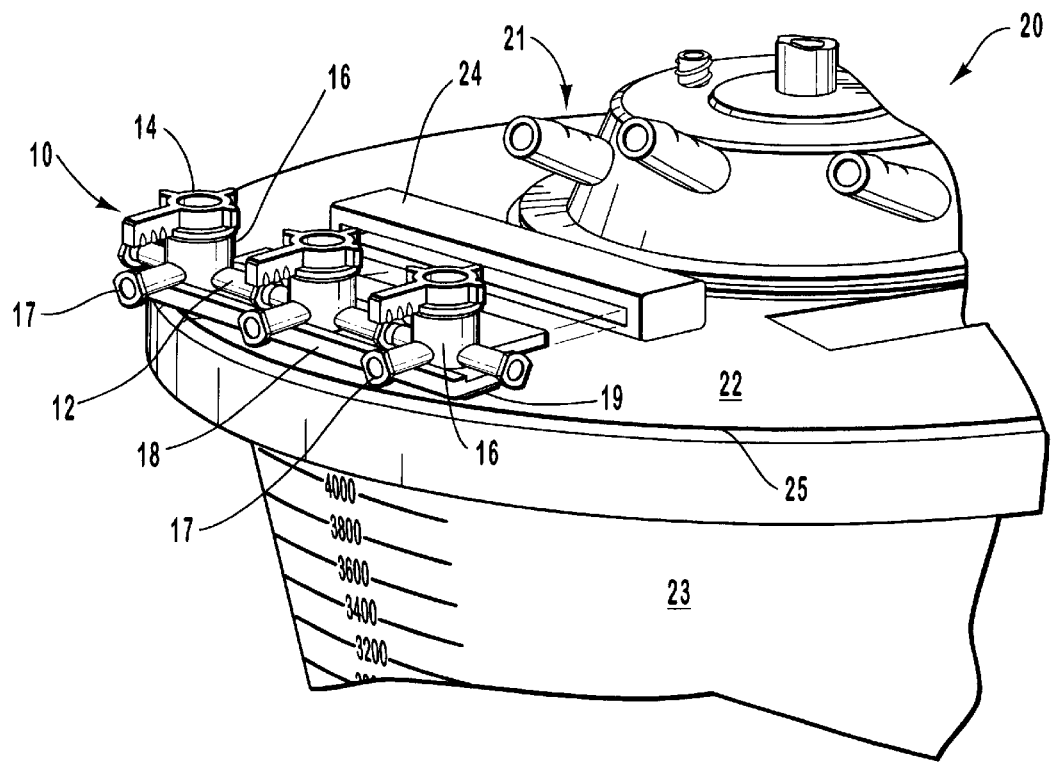
FIG. 1 is a view of a manifold of the prior art shown adjacent a socket of a venous reservoir of the prior art.
Figure 2:
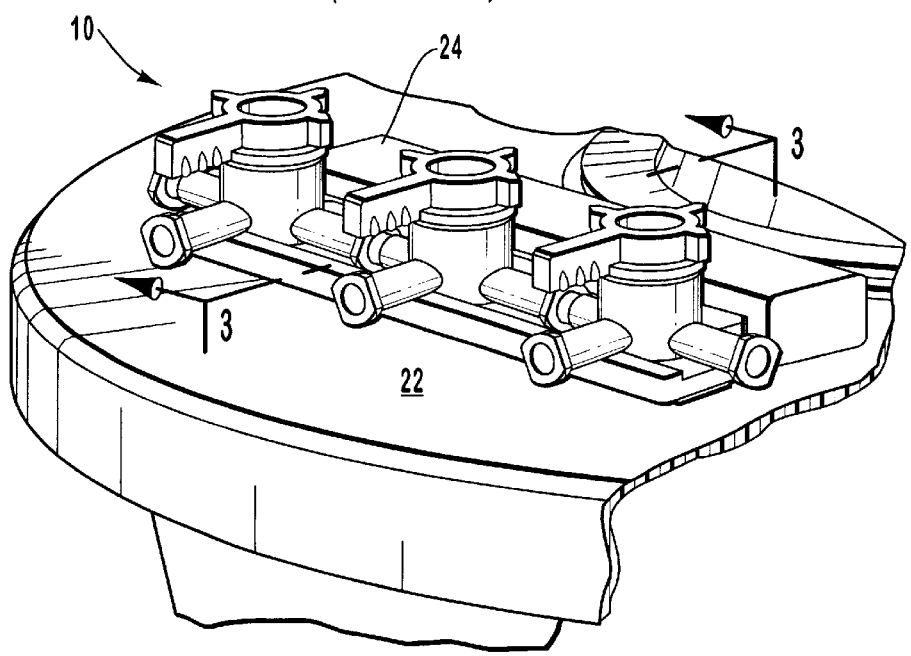
FIG. 2 is a view of the manifold of FIG. 1 having a plate thereof positioned within the socket of the venous reservoir.
Figure 3:
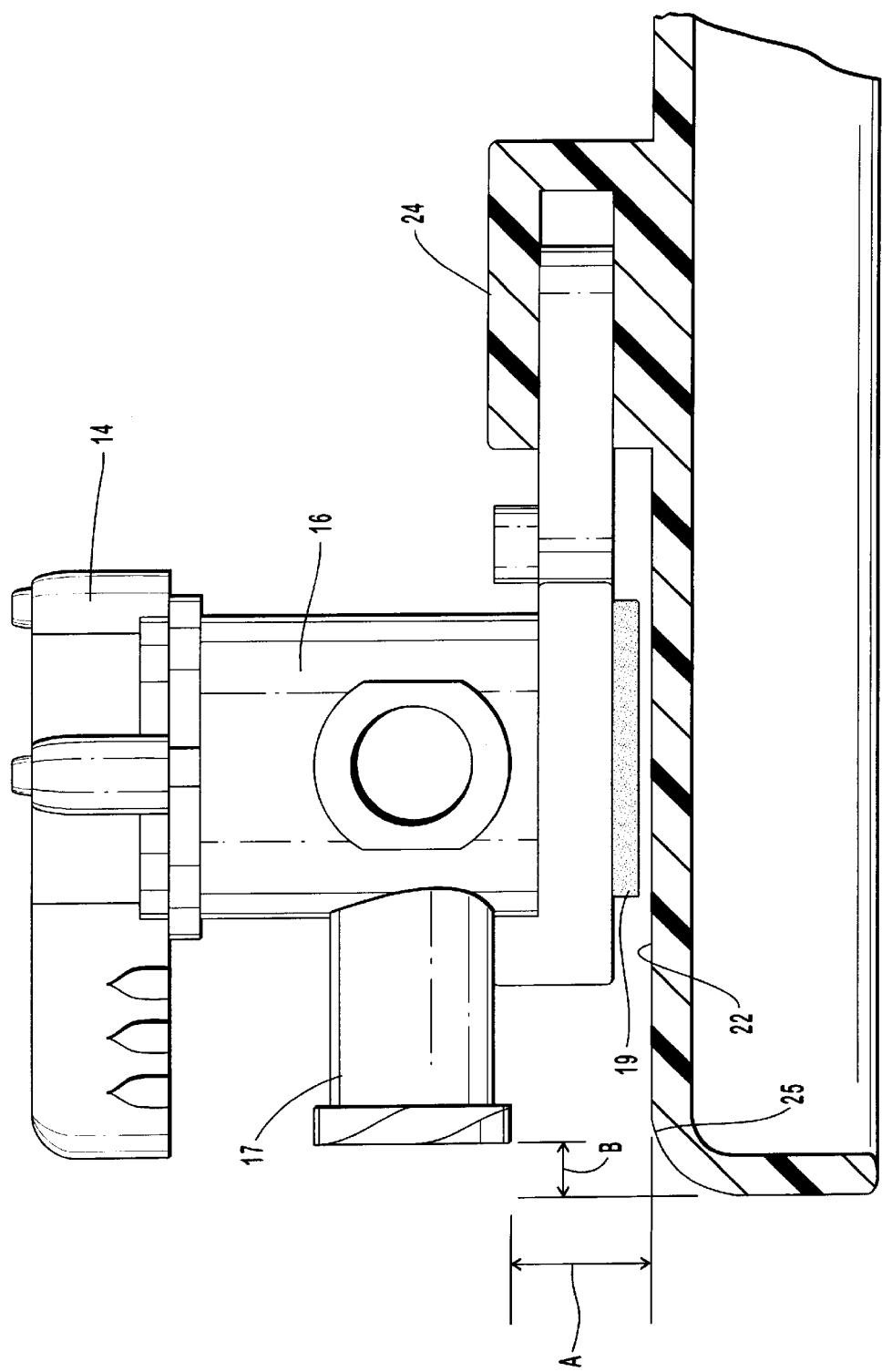
FIG. 3 is a cross sectional cutaway side view of the manifold, socket and venous reservoir of FIG. 2.
Figure 8:
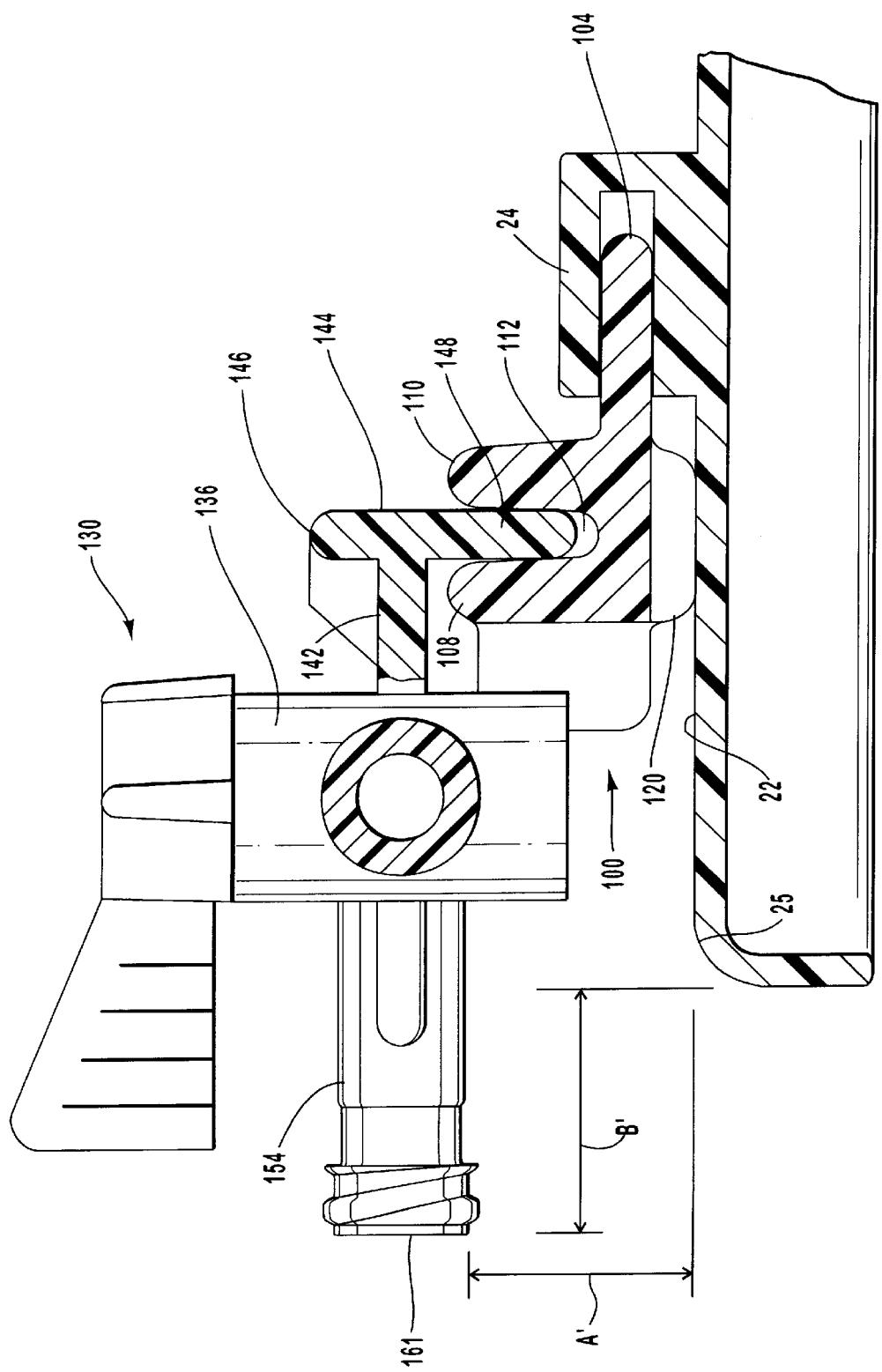
FIG. 8 is a cross sectional cutaway side view of the manifold, adaptor bracket, socket and venous reservoir of FIG. 7.

With reference now to FIG. 8, adaptor bracket 100 is shown as selectively coupling manifold 130 to socket 24. As shown in FIG. 8, by positioning a side of flange 144 or other portion of a manifold within gripping fingers 108, 110, manifold 130 is raised significantly from the surface of an object, allowing convenient manipulation of the ports and valves of manifold 130. Note that the distance A' between port 154 and lid 22 of FIG. 8 is significantly greater than the distance A between port 17 and lid 22 of FIG. 3. In addition, note that port face 161 of FIG. 8 is extended outwardly away from peripheral edge 25 of FIG. 8 by a distance of B', while the port face 19 of port 17 is extended inwardly away from edge 25 by a distance of B.

Thus, as illustrated in FIGS. 7 and 8, adaptor bracket 100 extends the faces 170, 161, 174 of at least the front ports of manifold 130 vertically and horizontally away from peripheral edge 25 of lid 22. Adaptor bracket 100 also extends the faces 176, 178 of the side ports of manifold 130 at least vertically away from peripheral edge 25 of lid 22, and possibly horizontally as well.

Since adaptor bracket 100 is selectively coupled to manifold 130, adaptor bracket 100 and manifold 130 can be made from different materials. For example, it may be desirable to manufacture adaptor bracket 100 from a lipid-compatible material such as polypropylene, while manufacturing manifold 130 from another material which does not require such compatibility. Since the fingers 108, 100 raise manifold 130 from the surface of an object, adaptor bracket 100 may be exposed to such lipids while manifold 130 is not exposed to the lipids. Another advantage of adaptor bracket 100 of the present invention, is that it can be retrofit onto a variety of different manifolds.

A receiving socket 24 may be configured integrally with a desired mounting object or may be coupled thereto through the use of an adhesive or a mechanical coupling, for example. Manifold 130, adaptor bracket 100, socket 24, and venous reservoir 20 are examples of a medical system which can be successfully employed in a variety of different settings.

It will thus be appreciated that one aspect of the invention relates to an adaptor bracket 100 for use in connecting a manifold device having a plurality of valves to a medical device, the medical device including a body and a lid attached to the body, the lid having a socket coupled to the lid adjacent a peripheral edge of the lid. An embodiment of adaptor bracket 100 comprises (i) means for receiving and vertically extending the manifold with respect to the surface of the lid; and (ii) means coupled to the socket and the means for receiving and vertically extending the manifold for horizontally extending the means for receiving and vertically extending the manifold with respect to the socket.

In the embodiment shown by way of example in FIGS. 4–8, the means for horizontally extending the means for receiving and vertically extending the manifold comprises a first tab portion 104 and the means for receiving and vertically extending the manifold with respect to a surface of the lid comprises (i) a second tab portion 106 coupled to first tab portion 104; and (ii) first and second gripping fingers 108, 110 extending from second tab portion 106, the first and second gripping fingers 108, 110 spaced so as to selectively receive a portion of the manifold within groove 112.

The second tab portion 106 and fingers 108, 110 thus combine to form a U-shaped member which extends a manifold such as manifold 130 vertically away from lid 22, thereby making access to manifold 130 more convenient. A tab member, such as first tab portion 104 is coupled to the U-shaped member, thereby extending the U-shaped member away from socket 24, also making access to manifold 130 more convenient.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An adaptor bracket for use in connecting a manifold device having a plurality of valves to a medical device, the medical device including a body and a lid attached to the body, the lid having a socket coupled to the lid, the adaptor bracket comprising:

means for receiving the manifold device in such a manner that the manifold device is vertically extended with respect to a surface of the lid; and means for coupling the receiving means to the socket of the lid in such a manner that the receiving means is horizontally extended with respect to the socket.

2. An adaptor bracket as recited in claim 1, wherein the means for horizontally extending the means for receiving and vertically extending the manifold comprises a first tab portion; and wherein the means for receiving the manifold comprises (i) a second tab portion coupled to a first tab portion; and (ii) first and second gripping fingers extending from the second tab portion, the first and second gripping fingers spaced so as to selectively receive a portion of the manifold within a groove formed between the first and second gripping fingers.

3. An adaptor bracket as recited in claim 2, wherein the first and second tab portions form an integral plate.

4. An adaptor bracket as recited in claim 2, wherein the first and second gripping fingers are configured to selectively receive a support member of the manifold device.

5. An adaptor bracket as recited in claim 4, wherein the gripping fingers receive the support member such that the manifold device is substantially parallel to the lid.

6. An adaptor bracket as recited in claim 2, further comprising a least one ridge located on an opposing side of the second tab portion from the first and second fingers.

7. An adaptor bracket as recited in claim 2, further comprising first and second ridges located on an opposing side of the second tab portion from the first and second fingers.

8. An adaptor bracket as recited in claim 2, wherein the first and second gripping fingers are configured to receive a portion of the manifold device in a tight-fitting relationship between them.

9. An adaptor bracket as recited in claim 1, wherein the means for coupling the receiving means comprises a tab portion configured to be selectively inserted within the socket of the lid.

10. An adaptor bracket as recited in claim 2, further comprising first and second aligning fingers extending from the receiving means and which serve to align the first and second gripping fingers with respect to at least one of the valves on the manifold.

11. An adaptor bracket for use in connecting a manifold device having a plurality of valves to a venous reservoir, the venous reservoir including a reservoir body and a lid attached to the reservoir body, the lid having a socket coupled to the lid adjacent a peripheral edge of the lid, the bracket comprising:

a tab having a first end and a second end, the first end being adapted for insertion into the socket; and first and second gripping fingers extending from the second end of the tab, the first and second gripping fingers spaced so as to selectively receive a portion of the manifold in a tight-fitting relationship within a groove formed between the first and second gripping fingers.

12. An adaptor bracket as recited in claim 11, further comprising first and second aligning fingers extending from the first gripping finger and which serve to align the first and second gripping fingers with respect to at least one of the valves on the manifold.

13. An adaptor bracket as recited in claim 11, further comprising first and second ridges located on an opposing side of the second end of the tab from the first and second fingers.

14. An adaptor bracket as recited in claim 11, wherein the first end of the tab is tapered on opposing edges thereof.

15. An adaptor bracket as recited in claim 11, wherein the first and second gripping fingers extend integrally from the tab.

16. An adaptor bracket for use in connecting a manifold device to a venous reservoir of a medical bypass system, the manifold having (i) a plurality of valves, each valve having at least one fluid flow port having a face; (ii) a support plate coupled to the plurality of valves; and (iii) a flange extending at approximately a right angle from the support plate, the venous reservoir including (i) a reservoir body; and (ii) a lid attached to the reservoir body, the lid having a socket coupled to the lid adjacent a peripheral edge of the lid, the bracket comprising:

a tab having a first end and a second end, the first end being adapted for insertion within the socket such that the tab is substantially parallel with the lid; and first and second gripping fingers extending from the second end of the tab, the first and second gripping fingers spaced so as to selectively receive the flange of the manifold within a groove formed between the first and second gripping fingers in a tight-fitting relationship, wherein the gripping fingers receive the flange of the manifold such that the support plate of the manifold is substantially parallel to the lid of the venous reservoir, and such that the bracket extends the face of at least one port on at least one of the valves of the manifold vertically and horizontally away from a peripheral edge of the lid.

17. An adaptor bracket as recited in claim 16, further comprising first and second aligning fingers extending from the first gripping finger and which serve to align the first and second gripping fingers with respect to at least one of the valves on the manifold.

18. A medical system, comprising:

a venous reservoir of a medical bypass system, the venous reservoir including (i) a reservoir body; and (ii) a lid attached to the reservoir body, the lid having a peripheral edge;

a socket coupled to the lid adjacent the peripheral edge of the lid;

a manifold having (i) a plurality of valves; and (ii) a support member coupled to the plurality of valves, each valve having at least one fluid flow port having a face; and an adaptor bracket for connecting the manifold to the venous reservoir, the bracket comprising:

a plate having a first end and a second end, the first end being configured to be selectively inserted within the receiving socket; and first and second gripping fingers extending from the second end of the plate, the first and second gripping fingers spaced so as to selectively receive the support member of the manifold within a groove formed between the first and second gripping fingers in a tight-fitting relationship, wherein the bracket extends the face of at least one port on at least one of the valves of the manifold vertically and horizontally away from a peripheral edge of the lid.

* * * * *